US008685659B2

(12) United States Patent
Zetter et al.

(10) Patent No.: US 8,685,659 B2
(45) Date of Patent: *Apr. 1, 2014

(54) METHOD FOR DIAGNOSIS AND PROGNOSIS OF EPITHELIAL CANCERS

(75) Inventors: Bruce R. Zetter, Wayland, MA (US); Adam S. Feldman, Brookline, MA (US); W. Scott McDougal, Manchester, MA (US)

(73) Assignees: Children's Medical Center Corporation, Boston, MA (US); The General Hospital Corporation, Boston, MA (US)

( * ) Notice: Subject to any disclaimer, the term of this patent is extended or adjusted under 35 U.S.C. 154(b) by 471 days.

This patent is subject to a terminal disclaimer.

(21) Appl. No.: 11/814,939

(22) PCT Filed: Jan. 30, 2006

(86) PCT No.: PCT/US2006/003049
§ 371 (c)(1),
(2), (4) Date: Jun. 3, 2009

(87) PCT Pub. No.: WO2006/081473
PCT Pub. Date: Aug. 3, 2006

(65) Prior Publication Data
US 2009/0239245 A1 Sep. 24, 2009

Related U.S. Application Data

(60) Provisional application No. 60/648,110, filed on Jan. 28, 2005.

(51) Int. Cl.
*G01N 33/574* (2006.01)

(52) U.S. Cl.
USPC ...................................................... 435/7.23

(58) Field of Classification Search
None
See application file for complete search history.

(56) References Cited

U.S. PATENT DOCUMENTS

| | | | |
|---|---|---|---|
| 4,281,061 A * | 7/1981 | Zuk et al. ................. | 435/7.9 |
| 6,998,232 B1 | 2/2006 | Feinstein et al. | |
| 2003/0157576 A1* | 8/2003 | Ervin, Jr. .................. | 435/7.23 |
| 2004/0076955 A1 | 4/2004 | Mack et al. | |
| 2004/0142361 A1* | 7/2004 | Dillon et al. ................ | 435/6 |

FOREIGN PATENT DOCUMENTS

| | | | |
|---|---|---|---|
| EP | 1 130 401 | A2 | 9/2001 |
| JP | 10-262680 | A | 10/1998 |
| JP | 2001-264329 | A | 9/2001 |
| JP | 2003-292459 | A | 10/2003 |
| WO | WO 2004/088324 | A2 | 10/2004 |
| WO | WO 2004/091383 | A2 | 10/2004 |
| WO | WO 2009/017475 | A2 | 2/2009 |

OTHER PUBLICATIONS

Levičar, Nataša et al., *Comparison of potential biological markers cathepsin B, cathepsin L, stefin A and stefin B with urokinase and plasminogen activator inhibitor-1 and clinicopathological data of breast carcinoma patients*, Cancer Detection and Prevention 26, pp. 42-49 (2002).
Shiraishi, Takeshi et al., *Identification of Cystatin B in Human Esophageal Carcinoma, Using Differential Displays In Which the Gene Expression is Related to Lymph-node Metastasis*, Int. J. Cancer (Pred. Oncol.), 79 pp. 175-178 (1998).
Extended Partial European Search Report from corresponding European Application No. 06 71 9762 dated Mar. 12, 2008.
Abrahamson, M. et al. "Isolation of six cysteine proteinase inhibitors from human urine, their physicochemical and enzyme kinetic properties and concentrations in biological fluids" Journal of Biological Chemistry, American Society of Biolochemical Biologists, Birmingham, US, vol. 261, No. 24, Jan. 1, 1986, pp. 11282-11289.
Mirtti Tuomas et al. "Expression of cystatins, high molecular weight cytokeratin, and proliferation markers in prostatic adenocarcinoma and hyperplasia" Prostate, Wiley-Liss, New York, NY, US, vol. 54, No. 4, Mar. 1, 2003, pp. 290-298.
Dippold Wolfgang G. et al. "A common epithelial cell surface antigen (EPM-1) on gastrointestinal tumors and in human sera" Cancer Research, American Association for Cancer Research, Baltimore, MD.; US, vol. 47, Jul. 15, 1987, pp. 3873-3879.
Kastelic L. et al. "Stefin B, the major low molecular weight inhibitor in ovarian carcinoma" Cancer Letters, New York, NY, US, vol. 82, No. 1, Jul. 15, 1994, pp. 81-88.
Shariat et al. "Urine Detection of Survivin is a Sensitive Marker for the Noninvasive Diagnosis of Bladder Cancer" Journal of Urology, Baltimore, MD, US, vol. 171, No. 2, Feb. 1, 2004, pp. 626-630.
Guo et al., A strategy for high-resolution protein identification in surface-enhanced laser desorption/ionization mass spectrometry: calgranulin A and chaperonin 10 as protein markers for endometrial carcinoma. Proteomics. May 2005;5(7):1953-66.
Kluger et al., cDNA microarray analysis of invasive and tumorigenic phenotypes in a breast cancer model. Lab Invest. Mar. 2004;84(3):320-31.
Zhang et al., Expression patterns of esophageal cancer deregulated genes in C57BL/6J mouse embryogenesis. World J Gastroenterol. Apr. 15, 2004;10(8):1088-92.
Zou et al., Exploring profilin as a target for suppressing the migration of breast cancer cells. Proc Amer Assoc Cancer Res. Apr. 2006;47:1013.
Kos et al., Cysteine proteinase inhibitors stefin A, stefin B, and cystatin C in sera from patients with colorectal cancer: relation to prognosis. Clin Cancer Res. Feb. 2000;6(2):505-11.

* cited by examiner

*Primary Examiner* — Sheela J Huff
(74) *Attorney, Agent, or Firm* — Wolf, Greenfield & Sacks, P.C.

(57) ABSTRACT

The present invention is based on the discovery that three proteins, Cystatin B, Chaperonin 10, and Profilin are present in the urine of patients with bladder cancer, a cancer of epithelial origin. Accordingly, the present invention is directed to methods for prognostic evaluation of cancers of epithelial origin and to methods for facilitating diagnosis of cancers of epithelial origin by monitoring the presence of these markers in biological samples. The invention is also directed to markers for therapeutic efficacy.

19 Claims, 3 Drawing Sheets

COMPARITIVE 2D-PAGE OF INVASIVE BLADDER TUMOR TISSUE AND NORMAL BLADDER TISSUE AND NORMAL BLADDER TISSUE REVEALS MANY POTENTIAL SPOTS. THE CIRCLED SPOT, WAS IDENTIFIED BY MASS SPECTROSCOPY TO BE CYSTATIN B.

METHOD FOR DIAGNOSIS AND PROGNOSIS OF EPITHELIAL CANCERS

CROSS-REFERENCE TO RELATED APPLICATION

This application is the national stage of International (PCT) Patent Application Serial No. PCT/US2006/003049, filed Jan. 30, 2006, and published under PCT Article 21(2) in English, which claims priority to and the benefit under 35 U.S.C. §119(e) of U.S. provisional Patent Application No. 60/648,110 filed Jan. 28, 2005; the contents of each application are incorporated herein by reference in their entirety.

GOVERNMENT SUPPORT

This work was supported by National Institute of Health grant number 2R37 CA37393. The government has certain rights to the invention.

BACKGROUND OF THE INVENTION

One of the most important factors in the survival of cancer is detection at an early stage. Clinical assays that detect the early events of cancer offer an opportunity to intervene and prevent cancer progression. With the development of gene profiling and proteomics there has been significant progress in the identification of molecular markers or "biomarkers" that can be used to diagnose and prognose specific cancers. For example, in the case of prostate cancer, the antigen PSA (for prostate specific antigen) can be detected in the blood and is indicative of the presence of prostate cancer. Thus, the blood of men at risk for prostate cancer can be quickly, easily, and safely screened for elevated PSA levels.

Even though there has been significant progress in the field of cancer detection, there still remains a need in the art for the identification of new biomarkers for a variety of cancers that can be easily used in clinical applications. For example, to date there are relatively few options available for the diagnosis of breast cancer using easily detectable biomarkers. Overexpression of EGFR, particularly coupled with down-regulation of the estrogen receptor, is a marker of poor prognosis in breast cancer patients. Other known markers of breast cancer include high levels of M2 pyruvate kinase (M2 PK) in blood (U.S. Pat. No. 6,358,683), high ZNF217 protein levels in blood (WO 98/02539), and differential expression of a newly identified protein in breast cancer, PDEBC, which is useful for diagnosis (U.S. patent application No. 20030124543). Cell surface markers such as CEA, CA-125 and HCG are frequently elevated in the serum of patients with locally advanced and metastatic bladder cancer (Izes et al., J. Urol. June; 165(6 Pt 1):1908-13, 2001), and studies involving circulating levels of tumor-related proteins such as matrix metalloproteinase-2 (Gohji et al., Cancer Research 56:3196, 1996), hepatocyte growth factor (Gohji et al., J. Clin. Oncol. 18:2963, 2000), and tissue polypeptide antigen (Maulard-Durdux et al., J. Clin. Oncol. 15:3446, 1997) have shown promise. These biomarkers offer alternative methods of diagnosis, however, they are not widely used. Furthermore, despite the use of a number of histochemical, genetic, and immunological markers, clinicians still have a difficult time predicting which tumors will metastasize to other organs.

The identification of cancer biomarkers is particularly relevant to improving diagnosis, prognosis, and treatment of the disease. As such, there is need in the art to identify alternative biomarkers that can be quickly, easily, and safely detected. Such biomarkers may be used to diagnose, to stage, or to monitor the progression or treatment of a subject with bladder cancer, in particular, an invasive, potentially metastatic stage of the disease.

SUMMARY OF THE INVENTION

The present invention is based on the surprising discovery that three proteins, Cystatin B, Chaperonin 10, and Profilin (also referred to as "epithelial cancer markers"), are present in the urine of patients with bladder cancer, a cancer of epithelial origin. Accordingly, the present invention is directed to methods for prognostic evaluation of cancers of epithelial origin and to methods for facilitating diagnosis of cancers of epithelial origin by monitoring the presence of these markers in biological samples. The invention is also directed to markers for therapeutic efficacy. In particular, the amount of Cystatin B detected in urine correlates with disease status such that Cystatin B levels can be used to predict the presence of invasive bladder cancer. Thus, measuring the level of Cystatin B, Chaperonin 10, and/or Profilin proteins in urine provides a quick, easy, and safe screen that can be used to both diagnose and prognose bladder cancer in a patient. Alternatively, the absence of these markers can provide an indication that the patient does not have bladder cancer.

In one embodiment, a method for facilitating the diagnosis of cancer of an epithelial origin in a patient is provided. The method comprises obtaining a biological sample, preferably a voided urine specimen, from a patient and detecting the presence or absence of at least one epithelial cancer biomarker (Cystatin B, Chaperonin 10, or Profilin) in the sample, wherein the presence of at least one epithelial cancer biomarker is indicative of cancer of epithelial origin.

Biological samples, for example, can be obtained from blood, tissue (e.g. tumor or breast), serum, stool, urine, sputum, cerebrospinal fluid, nipple aspirates and supernatant from cell lysate. One preferred biological sample is urine.

As used herein, "cancer of epithelial origin" refers to cancers that arise from epithelial cells which include, but are not limited to, breast cancer, basal cell carcinoma, adenocarcinoma, gastrointestinal cancer, lip cancer, mouth cancer, esophageal cancer, small bowel cancer and stomach cancer, colon cancer, liver cancer, bladder cancer, pancreas cancer, ovary cancer, cervical cancer, lung cancer, breast cancer and skin cancer, such as squamous cell and basal cell cancers, prostate cancer, renal cell carcinoma, and other known cancers that effect epithelial cells throughout the body.

In one embodiment, a method for facilitating the diagnosis of bladder cancer in a patient is provided. The method comprises obtaining a biological sample, preferably a voided urine specimen, from a patient and detecting the presence or absence of at least one epithelial cancer biomarker (Cystatin B, Chaperonin 10, or Profilin) in urine sample, wherein the presence of at least one epithelial cancer biomarker is indicative of bladder cancer.

In another embodiment, the method for diagnosing a cancer of epithelial origin is provided. The comprises measuring the level of at least one epithelial cancer biomarker present in a biological sample (test sample) from a patient and comparing the observed level of at least one marker (Cystatin B, Chaperonin 10, or Profilin) with the level of the marker present in a control sample of the same type. Higher levels of markers in the test sample, as compared to the control sample, is indicative of cancer of epithelial origin.

In one preferred embodiment, the methods of the invention are used for early detection of cancer. For example, a patient can be screened by a physician during their physical.

In one embodiment, a method for diagnosing bladder cancer is provided. The method comprises measuring the level of at least one epithelial cancer biomarker (Cystatin B, Chaperonin 10, or Profilin) present in a biological sample (the test sample) from a patient and comparing the observed level of at least one marker with the level of the marker present in a control sample of the same type. Higher levels of markers in the test sample, as compared to the control sample, is indicative of bladder cancer.

In one embodiment, a method for diagnosing invasive bladder cancer in a patient is provided. The method comprises measuring levels of Cystatin B epithelial cancer biomarker present in a biological sample obtained from the patient (test sample) and comparing the level of Cystatin B in the test sample with the level of Cystatin B present in a non-invasive cancer control sample. A higher level of Cystatin B in the test sample as compared to the level of Cystatin B in the control sample is indicative of invasive bladder cancer.

The term "control sample" refers to a biological sample (e.g. blood, urine, tumor) obtained from a "normal" or "healthy" individual(s) that is believed not to have cancer. Controls may be selected using methods that are well known in the art. Once a level has become well established for a control population, array results from test biological samples can be directly compared with the known levels.

The term "non-invasive control sample" refers to a biological sample obtained from a individual(s) that has a non-invasive form of cancer. Once a level has become well established for a control population, array results from test biological samples can be directly compared with the known levels.

The term "test sample" refers to a biological sample obtained from a patient being tested for a cancer of epithelial origin.

The present invention also contemplates the assessment of the level of epithelial cancer biomarker present in multiple test samples obtained from the same patient, where a progressive increase in the amount of the marker over time indicates an increased aggressiveness (e.g. metastatic potential) of the cancer tumor. As such, the levels of the epithelial cancer biomarker serve as a predictor of disease status and stage.

The present invention further contemplates the assessment of epithelial cancer biomarker/s to monitor the therapeutic efficacy of a treatment regime designed to treat a patient having a cancer of epithelial origin (e.g. bladder cancer).

In one aspect of the invention, epithelial cancer biomarker levels (e.g. (Cystatin B, Chaperonin 10, or Profilin) present in a test biological sample are measured by contacting the test sample, or preparation thereof, with an antibody-based binding moiety that specifically binds to the epithelial cancer biomarker, or to a portion thereof.

Antibody-based immunoassays are the preferred means for measuring levels of biomarkers. However, any means known to those skilled in art can be used to assess biomarker levels. For example, biomarker levels can be assessed by mass spectrometry, including SELDI mass spectrometry.

In a further embodiment, the invention provides for kits that comprise means for measuring at least one epithelial cancer biomarker in a biological sample. The kit comprises a container for holding a biological sample (e.g. urine sample), and at least one antibody that specifically binds an epithelial cancer biomarker.

In one embodiment, the kit provides comprises two antibodies that specifically binds to an epithelial cancer biomarker. In one embodiment, one antibody is immobilized on a solid phase and one antibody is detectably labeled. The kits can comprise can comprise anti-Cystatin B, anti-Chaperonin 10, and/or anti-Profilin antibodies.

Other aspects of the invention are disclosed infra.

BRIEF DESCRIPTION OF THE DRAWINGS

The accompanying drawings, which are incorporated in and constitute a part of this specification, illustrate embodiments of the invention and, together with the description, serve to explain the objects, advantages, and principles of the invention.

DETAILED DESCRIPTION OF THE INVENTION

Figure 1:
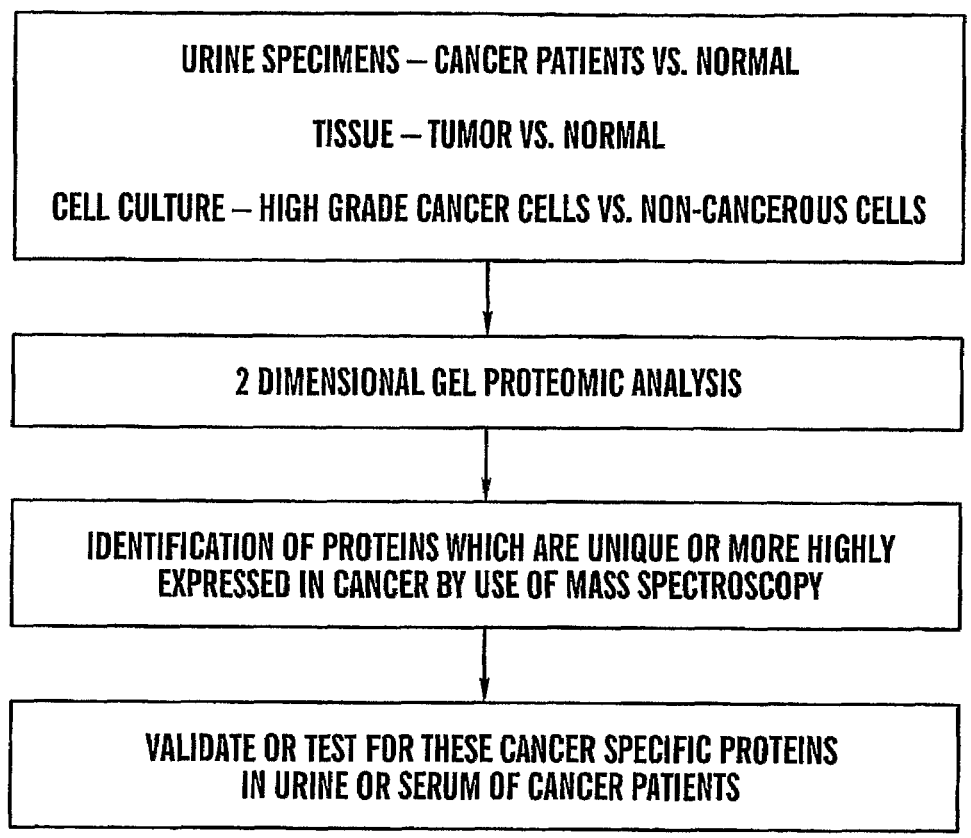
FIG. 1 is a flow diagram showing the approach to epithelial cancer biomarker discovery.
Figure 2:
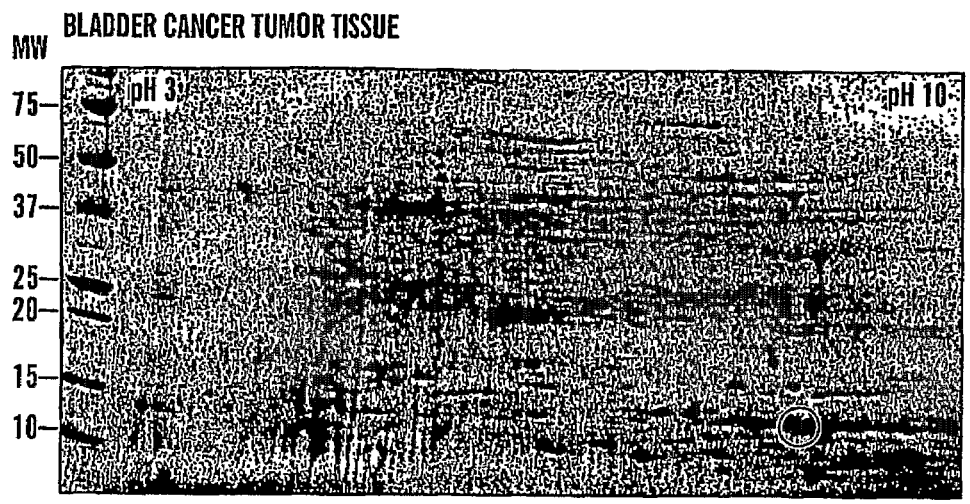
FIG. 2 shows comparative 2D page of invasive bladder tumor tissue and normal bladder tissue reveals many potential spots. The circled spot was identified by mass spectroscopy to be Cystatin B.
Figure 2:
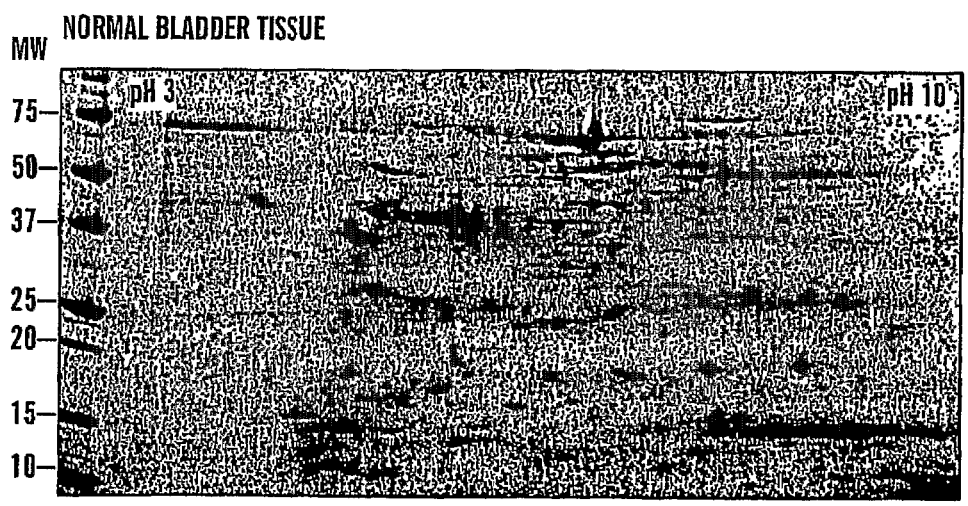
Figure 3:
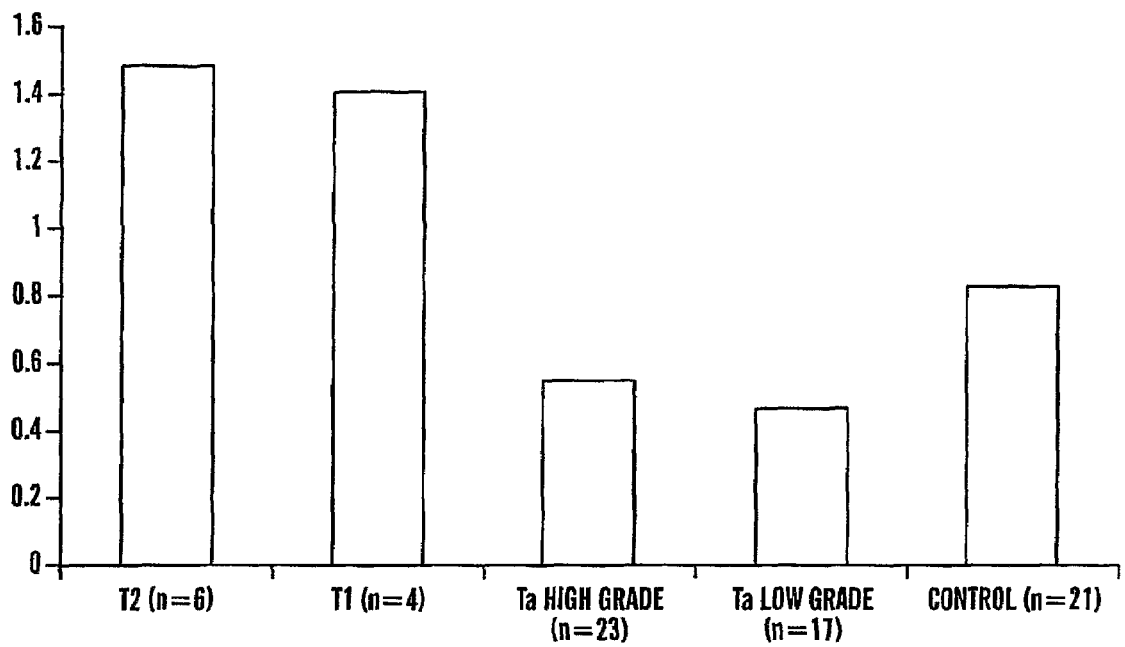
FIG. 3 shows a graph depicting the results of a semi-quantitative Western Blot analysis of Cystatin B detected in voided urine specimens.

We have discovered that three proteins, Cystatin B, Chaperonin 10, and Profilin (referred to herein as "epithelial cancer markers"), are present in the urine of patients that have cancers of epithelial origin. Levels of Cystatin B present in urine samples of patients correlate with the presence of bladder cancers, in particular invasive bladder cancers.

The term "aggressive" or "invasive" with respect to cancer refers to the proclivity of a tumor for expanding beyond its boundaries into adjacent tissue (Darnell, J. (1990), Molecular Cell Biology, Third Ed., W. H. Freeman, NY). Invasive cancer can be contrasted with organ-confined cancer wherein the tumor is confined to a particular organ. The invasive property of a tumor is often accompanied by the elaboration of proteolytic enzymes, such as collagenases, that degrade matrix material and basement membrane material to enable the tumor to expand beyond the confines of the capsule, and beyond confines of the particular tissue in which that tumor is located. Invasive bladder cancer includes invasive into Muscularis Propria and/or Lamina Propria.

The term "metastasis", as used herein, refers to the condition of spread of cancer from the organ of origin to additional distal sites in the patient. The process of tumor metastasis is a multistage event involving local invasion and destruction of intercellular matrix, intravasation into blood vessels, lymphatics or other channels of transport, survival in the circulation, extravasation out of the vessels in the secondary site and growth in the new location (Fidler, et al., Adv. Cancer Res. 28, 149-250 (1978), Liotta, et al., Cancer Treatment Res. 40, 223-238 (1988), Nicolson, Biochim. Biophy. Acta 948, 175-224 (1988) and Zetter, N. Eng. J. Med. 322, 605-612 (1990)). Increased malignant cell motility has been associated with enhanced metastatic potential in animal as well as human tumors (Hosaka, et al., Gann 69, 273-276 (1978) and Haemmerlin, et al., Int. J. Cancer 27, 603-610 (1981)).

As used herein, a "biological sample" refers to a urine sample obtained from a patient. Biological samples, for example, can be obtained from blood, tissue (e.g. tumor or breast), serum, stool, urine, sputum, cerebrospinal fluid, nipple aspirates and supernatant from cell lysate. One preferred biological sample is urine.

In a preferred embodiment, the biological sample is treated as to prevent degradation of epithelial cancer biomarkers. Methods for inhibiting or preventing degradation include, but are not limited to, treatment of the sample with protease, freezing the sample, or placing the sample on ice. Preferably, prior to analysis, the samples are constantly kept under conditions as to prevent degradation of the markers.

As used herein, a "tumor sample" refers to a portion, piece, part, segment, or fraction of a tumor, for example, a tumor which is obtained or removed from a subject (e.g., removed or extracted from a tissue of a subject), preferably a human subject.

As used herein, Cystatin B refers to the protein of Genebank accession NM_000100.2, NP_000091 (*Homosapiens*). The term also encompasses species variants, homologues, allelic forms, mutant forms, and equivalents thereof.

As used herein, Chaperonin 10 refers to the protein of Genebank accession, protein, AAA50953 (*Homosapiens*). The term also encompasses species variants, homologues, allelic forms, mutant forms, and equivalents thereof.

As used herein, Profilin refers to the protein of Genebank accession, protein, A28622 (*Homosapiens*). The term also encompasses species variants, homologues, allelic forms, mutant forms, and equivalents thereof.

The present invention is directed to methods for facilitating diagnosis of cancers of epithelial origin in a patient. In one embodiment, the method comprises obtaining a biological sample from a patient and detecting the presence or absence of at least one epithelial cancer biomarker (Cystatin B, Chaperonin 10, or Profilin) in the sample, wherein the presence of at least one marker is indicative of the presence of cancer of epithelial origin.

In another embodiment, the methods involve measuring levels of at least one epithelial cancer biomarker (Cystatin B, Chaperonin 10, or Profilin) in a test sample obtained from a patient being tested for cancer, and comparing the observed levels to the levels of the epithelial cancer biomarker found in a control sample, for example a sample obtained from an individual patient or population of individuals that do not to have cancer. Levels of at least one epithelial cancer biomarker higher than levels that are observed in the normal control indicate the presence of cancer of epithelial origin. The levels of biomarkers can be represented by arbitrary units, for example as units obtained from a densitometer, luminometer, or an Elisa plate reader.

As used herein, "a higher level of at least one epithelial cancer biomarker in the test sample as compared to the level in the control sample" refers to an amount of at least one biomarker that is greater than an amount of the same biomarker present in a control sample. The term "higher level" refers to a level that is statistically significant or significantly above levels found in the control sample. The "higher level" can be for example 1.2 fold to 1.9 fold higher. Preferably, the "higher level" is at least 2 fold greater, or even 3 fold greater.

The term "statistically significant" or "significantly" refers to statistical significance and generally means a two standard deviation (2SD) above normal, or higher, concentration of the marker.

For purposes of comparison, the test sample and control sample are of the same type, that is, obtained from the same biological source. The control sample can also be a standard sample that contains the same concentration of the epithelial cancer biomarker that is normally found in a biological sample that is obtained from a healthy individual.

In one aspect of the invention, a secondary diagnostic step can be performed. For example, if a level of at least one epithelial cancer biomarker is found to indicate the presence of cancer, then an additional method of detecting the cancer can be performed to confirm the presence of the cancer. Any of a variety of additional diagnostic steps can be used, such as ultrasound, PET scanning, MRI, or any other imaging techniques, biopsy, clinical examination, ductogram, or any other method.

The present invention further provides for methods of prognostic evaluation of a patient suspected of having, or having, cancer of epithelial origin. The method comprises measuring the level of at least one epithelial cancer biomarker (Cystatin B, Chaperonin 10, or Profilin) present in a test biological sample obtained from a patient and comparing the observed level with a range of at least one epithelial cancer biomarker levels normally found in biological samples (of the same type) of healthy individuals. A high level for example, is indicative of a greater potential for metastatic activity and corresponds to a poor prognosis, while lower levels indicate that the tumor is less aggressive and correspond to a better prognosis.

Additionally, disease progression can be assessed by following the levels of at least one epithelial cancer biomarker in an individual patient. For example, changes in the patients condition can be monitored by comparing changes expression levels of Cystatin B, Chaperonin 10, or Profilin in the patient over time. Progressive increases in the levels of at least one epithelial cancer biomarker is indicative of increased potential for tumor invasion and metastasis.

The prognostic methods of the invention also are useful for determining a proper course of treatment for a patient having cancer. A course of treatment refers to the therapeutic measures taken for a patient after diagnosis or after treatment for cancer. For example, a determination of the likelihood for cancer recurrence, spread, or patient survival, can assist in determining whether a more conservative or more radical approach to therapy should be taken, or whether treatment modalities should be combined. For example, when cancer recurrence is likely, it can be advantageous to precede or follow surgical treatment with chemotherapy, radiation, immunotherapy, biological modifier therapy, gene therapy, vaccines, and the like, or adjust the span of time during which the patient is treated.

The methods of the invention are suitable to diagnose or prognose any cancer of epithelial origin, including but not limited to, breast cancer, basal cell carcinoma, adenocarcinoma, gastrointestinal cancer, lip cancer, mouth cancer, esophageal cancer, small bowel cancer and stomach cancer, colon cancer, liver cancer, bladder cancer, pancreas cancer, ovary cancer, cervical cancer, lung cancer, breast cancer and skin cancer, such as squamous cell and basal cell cancers, prostate cancer, renal cell carcinoma, and other known cancers that effect epithelial cells throughout the body.

In one preferred embodiment, the cancer of epithelial origin is bladder cancer.

Measuring Levels of at Least One Epithelial Cancer Biomarker

The levels of at least one epithelial cancer biomarker, as described herein, can be measured by any means known to those skilled in the art. In the present invention, it is generally preferred to use antibodies, or antibody equivalents, to detect levels of at least one epithelial cancer biomarker protein in biological samples.

In one embodiment, levels of at least one epithelial cancer biomarker protein are measured by contacting the biological sample with an antibody-based binding moiety that specifically binds to at least one epithelial cancer biomarker, or to a fragment of at least one epithelial cancer biomarker. Formation of the antibody-epithelial cancer biomarker complex is then detected as a measure of the epithelial cancer biomarker levels.

The term "antibody-based binding moiety" or "antibody" includes immunoglobulin molecules and immunologically active determinants of immunoglobulin molecules, e.g., molecules that contain an antigen binding site which specifically binds (immunoreacts with) to the epithelial cancer biomarker to be detected, e.g. Cystatin B, Chaperonin 10, or Profilin. The term "antibody-based binding moiety" is intended to include whole antibodies, e.g., of any isotype (IgG, IgA, IgM, IgE, etc), and includes fragments thereof which are also specifically reactive the epithelial cancer biomarker protein. Antibodies can be fragmented using conventional techniques. Thus, the term includes segments of proteolytically-cleaved or recombinantly-prepared portions of an antibody molecule that are capable of selectively reacting with a certain protein. Non limiting examples of such proteolytic and/or recombinant fragments include Fab, F(ab')2, Fab', Fv, dAbs and single chain antibodies (scFv) containing a VL and VH domain joined by a peptide linker. The scFv's may be covalently or non-covalently linked to form antibodies having two or more binding sites. Thus, "antibody-base binding moiety" includes polyclonal, monoclonal, or other purified preparations of antibodies and recombinant antibodies. The term "antibody-base binding moiety" is further intended to include humanized antibodies, bispecific antibodies, and chimeric molecules having at least one antigen binding determinant derived from an antibody molecule. In a preferred embodiment, the antibody-based binding moiety detectably labeled.

"Labeled antibody", as used herein, includes antibodies that are labeled by a detectable means and include, but are not limited to, antibodies that are enzymatically, radioactively, fluorescently, and chemiluminescently labeled. Antibodies can also be labeled with a detectable tag, such as c-Myc, HA, VSV-G, HSV, FLAG, V5, or HIS.

In the diagnostic and prognostic methods of the invention that use antibody based binding moieties for the detection of at least one epithelial cancer biomarker, the level of at least one epithelial cancer biomarker present in the biological samples correlate to the intensity of the signal emitted from the detectably labeled antibody.

In one preferred embodiment, the antibody-based binding moiety is detectably labeled by linking the antibody to an enzyme. The enzyme, in turn, when exposed to it's substrate, will react with the substrate in such a manner as to produce a chemical moiety which can be detected, for example, by spectrophotometric, fluorometric or by visual means. Enzymes which can be used to detectably label the antibodies of the present invention include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase. Chemiluminescence is another method that can be used to detect an antibody-based binding moiety.

Detection may also be accomplished using any of a variety of other immunoassays. For example, by radioactively labeling an antibody, it is possible to detect the antibody through the use of radioimmune assays. The radioactive isotope can be detected by such means as the use of a gamma counter or a scintillation counter or by audoradiography. Isotopes which are particularly useful for the purpose of the present invention are $^3$H, $^{131}$I, $^{35}$S, $^{14}$C, and preferably $^{125}$I.

It is also possible to label an antibody with a fluorescent compound. When the fluorescently labeled antibody is exposed to light of the proper wave length, its presence can then be detected due to fluorescence. Among the most commonly used fluorescent labeling compounds are CYE dyes, fluorescein isothiocyanate, rhodamine, phycoerytherin, phycocyanin, allophycocyanin, o-phthaldehyde and fluorescamine.

An antibody can also be detectably labeled using fluorescence emitting metals such as $^{152}$Eu, or others of the lanthanide series. These metals can be attached to the antibody using such metal chelating groups as diethylenetriaminepentaacetic acid (DTPA) or ethylenediaminetetraacetic acid (EDTA).

An antibody also can be detectably labeled by coupling it to a chemiluminescent compound. The presence of the chemiluminescent-antibody is then determined by detecting the presence of luminescence that arises during the course of a chemical reaction. Examples of particularly useful chemiluminescent labeling compounds are luminol, luciferin, isoluminol, theromatic acridinium ester, imidazole, acridinium salt and oxalate ester.

As mentioned above, levels of at least one epithelial cancer biomarker protein can be detected by immunoassays, such as enzyme linked immunoabsorbant assay (ELISA), radioimmunoassay (RIA), Immunoradiometric assay (IRMA), Western blotting, or immunohistochemistry, each of which are described in more detail below. Immunoassays such as ELISA or RIA, which can be extremely rapid, are more generally preferred. Antibody arrays or protein chips can also be employed, see for example U.S. Patent Application Nos: 20030013208A1; 20020155493A1; 20030017515 and U.S. Pat. Nos. 6,329,209; 6,365,418, which are herein incorporated by reference in their entirety.

Immunoassays

"Radioimmunoassay" is a technique for detecting and measuring the concentration of an antigen, biomarker to be detected, using a labeled (e.g. radioactively labeled) form of the antigen. Examples of radioactive labels for antigens include $^3$H, $^{14}$C, and $^{125}$I. The concentration of antigen in a biological sample is measured by having the antigen in the biological sample compete with the labeled (e.g. radioactively) antigen for binding to an antibody that specifically binds the antigen. To ensure competitive binding between the labeled antigen and the unlabeled antigen, the labeled antigen is present in a concentration sufficient to saturate the binding sites of the antibody. The higher the concentration of antigen in the sample, the lower the concentration of labeled antigen that will bind to the antibody.

In a radioimmunoassay, to determine the concentration of labeled antigen bound to antibody, the antigen-antibody complex must be separated from the free antigen. One method for separating the antigen-antibody complex from the free antigen is by precipitating the antigen-antibody complex with an anti-isotype antiserum. Another method for separating the antigen-antibody complex from the free antigen is by precipitating the antigen-antibody complex with formalin-killed *S. aureus*. Yet another method for separating the antigen-antibody complex from the free antigen is by performing a "solid-phase radioimmunoassay" where the antibody is linked (e.g., covalently) to Sepharose beads, polystyrene wells, polyvinylchloride wells, or microtiter wells. By comparing the concentration of labeled antigen bound to antibody to a standard curve based on samples having a known concentration of antigen, the concentration of antigen in the biological sample can be determined.

A "Immunoradiometric assay" (IRMA) is an immunoassay in which the antibody reagent is radioactively labeled. An IRMA requires the production of a multivalent antigen conjugate, by techniques such as conjugation to a protein e.g., rabbit serum albumin (RSA). The multivalent antigen conjugate must have at least 2 antigen residues per molecule and the antigen residues must be of sufficient distance apart to allow binding by at least two antibodies to the antigen. For example, in an IRMA the multivalent antigen conjugate can be attached to a solid surface such as a plastic sphere. Unlabeled "sample" antigen and antibody to antigen which is radioactively labeled are added to a test tube containing the multivalent antigen conjugate coated sphere. The antigen in the sample competes with the multivalent antigen conjugate for antigen antibody binding sites. After an appropriate incubation period, the unbound reactants are removed by washing and the amount of radioactivity on the solid phase is determined. The amount of bound radioactive antibody is inversely proportional to the concentration of antigen in the sample.

The most common enzyme immunoassay is the "Enzyme-Linked Immunosorbent Assay (ELISA)." ELISA is a technique for detecting and measuring the concentration of an antigen using a labeled (e.g. enzyme linked) form of the antibody. There are different forms of ELISA, which are well known to those skilled in the art. The standard techniques known in the art for ELISA are described in "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. 1984, J. Clin. Chem. Clin. Biochem., 22:895-904.

In a "sandwich ELISA", an antibody (e.g. anti-cystatin B, anti-chaperonin 10, or anti-profilin) is linked to a solid phase (i.e. a microtiter plate) and exposed to a biological sample containing antigen (e.g. cystatin B, chaperonin 10, and/or profilin). The solid phase is then washed to remove unbound antigen. A labeled antibody (e.g. enzyme linked) is then bound to the bound-antigen (if present) forming an antibody-antigen-antibody sandwich. Examples of enzymes that can be linked to the antibody are alkaline phosphatase, horseradish peroxidase, luciferase, urease, and B-galactosidase. The enzyme linked antibody reacts with a substrate to generate a colored reaction product that can be measured.

In a "competitive ELISA", antibody is incubated with a sample containing antigen (i.e. at least one epithelial cancer biomarker). The antigen-antibody mixture is then contacted with a solid phase (e.g. a microtiter plate) that is coated with antigen (i.e., at least one epithelial cancer biomarker). The more antigen present in the sample, the less free antibody that will be available to bind to the solid phase. A labeled (e.g., enzyme linked) secondary antibody is then added to the solid phase to determine the amount of primary antibody bound to the solid phase.

In a "immunohistochemistry assay" a section of tissue is tested for specific proteins by exposing the tissue to antibodies that are specific for the protein that is being assayed. The antibodies are then visualized by any of a number of methods to determine the presence and amount of the protein present. Examples of methods used to visualize antibodies are, for example, through enzymes linked to the antibodies (e.g., luciferase, alkaline phosphatase, horseradish peroxidase, or .beta.-galactosidase), or chemical methods (e.g., DAB/Substrate chromagen). It is also contemplated that tissue microarrays can be used in methods of the invention.

Other techniques may be used to detect at least one epithelial cancer biomarker, according to a practitioner's preference, based upon the present disclosure. One such technique is Western blotting (Towbin et al., Proc. Nat. Acad. Sci. 76:4350 (1979)), wherein a suitably treated sample is run on an SDS-PAGE gel before being transferred to a solid support, such as a nitrocellulose filter. Detectably labeled anti-biomarker antibodies can then be used to assess the levels of at least one epithelial cancer biomarker, where the intensity of the signal from the detectable label corresponds to the amount biomarker present. Levels can be quantitated, for example by densitometry.

Mass Spectometry

In addition, at least one epithelial cancer biomarker may be detected using Mass Spectrometry such as MALDI/TOF (time-of-flight), SELDI/TOF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, or tandem mass spectrometry (e.g., MS/MS, MS/MS/MS, ESI-MS/MS, etc.). See for example, U.S. Patent Application Nos: 20030199001, 20030134304, 20030077616, which are herein incorporated by reference.

Mass spectrometry methods are well known in the art and have been used to quantify and/or identify biomolecules, such as proteins (see, e.g., Li et al. (2000) Tibtech 18:151-160; Rowley et al. (2000) Methods 20: 383-397; and Kuster and Mann (1998) Curr. Opin. Structural Biol. 8: 393-400). Further, mass spectrometric techniques have been developed that permit at least partial de novo sequencing of isolated proteins. Chait et al., Science 262:89-92 (1993); Keough et al., Proc. Natl. Acad. Sci. USA. 96:7131-6 (1999); reviewed in Bergman, EXS 88:133-44 (2000).

In certain embodiments, a gas phase ion spectrophotometer is used. In other embodiments, laser-desorption/ionization mass spectrometry is used to analyze the sample. Modern laser desorption/ionization mass spectrometry ("LDI-MS") can be practiced in two main variations: matrix assisted laser desorption/ionization ("MALDI") mass spectrometry and surface-enhanced laser desorption/ionization ("SELDI"). In MALDI, the analyte is mixed with a solution containing a matrix, and a drop of the liquid is placed on the surface of a substrate. The matrix solution then co-crystallizes with the biological molecules. The substrate is inserted into the mass spectrometer. Laser energy is directed to the substrate surface where it desorbs and ionizes the biological molecules without significantly fragmenting them. However, MALDI has limitations as an analytical tool. It does not provide means for fractionating the sample, and the matrix material can interfere with detection, especially for low molecular weight analytes. See, e.g., U.S. Pat. No. 5,118,937 (Hillenkamp et al.), and U.S. Pat. No. 5,045,694 (Beavis & Chait).

In SELDI, the substrate surface is modified so that it is an active participant in the desorption process. In one variant, the surface is derivatized with adsorbent and/or capture reagents that selectively bind the protein of interest. In another variant, the surface is derivatized with energy absorbing molecules that are not desorbed when struck with the laser. In another variant, the surface is derivatized with molecules that bind the protein of interest and that contain a photolytic bond that is broken upon application of the laser. In each of these methods, the derivatizing agent generally is localized to a specific location on the substrate surface where the sample is applied. See, e.g., U.S. Pat. No. 5,719,060 and WO 98/59361. The two methods can be combined by, for example, using a SELDI affinity surface to capture an analyte and adding matrix-containing liquid to the captured analyte to provide the energy absorbing material.

For additional information regarding mass spectrometers, see, e.g., Principles of Instrumental Analysis, 3rd edition, Skoog, Saunders College Publishing, Philadelphia, 1985; and Kirk-Othmer Encyclopedia of Chemical Technology, 4.sup.th ed. Vol. 15 (John Wiley & Sons, New York 1995), pp. 1071-1094.

Detection of the presence of a marker will typically involve detection of signal intensity. This, in turn, can reflect the quantity and character of a polypeptide bound to the substrate. For example, in certain embodiments, the signal strength of peak values from spectra of a first sample and a second sample can be compared (e.g., visually, by computer analysis etc.), to determine the relative amounts of particular biomolecules. Software programs such as the Biomarker Wizard program (Ciphergen Biosystems, Inc., Fremont, Calif.) can be used to aid in analyzing mass spectra. The mass spectrometers and their techniques are well known to those of skill in the art.

Any person skilled in the art understands, any of the components of a mass spectrometer (e.g., desorption source, mass analyzer, detect, etc.) and varied sample preparations can be combined with other suitable components or preparations described herein, or to those known in the art. For example, in some embodiments a control sample may contain heavy atoms (e.g. $^{13}C$) thereby permitting the test sample to mixed with the known control sample in the same mass spectrometry run.

In one preferred embodiment, a laser desorption time-of-flight (TOF) mass spectrometer is used. In laser desorption mass spectrometry, a substrate with a bound marker is introduced into an inlet system. The marker is desorbed and ionized into the gas phase by laser from the ionization source. The ions generated are collected by an ion optic assembly, and then in a time-of-flight mass analyzer, ions are accelerated through a short high voltage field and let drift into a high vacuum chamber. At the far end of the high vacuum chamber, the accelerated ions strike a sensitive detector surface at a different time. Since the time-of-flight is a function of the mass of the ions, the elapsed time between ion formation and ion detector impact can be used to identify the presence or absence of molecules of specific mass to charge ratio.

In some embodiments the relative amounts of one or more biomolecules present in a first or second sample is determined, in part, by executing an algorithm with a programmable digital computer. The algorithm identifies at least one peak value in the first mass spectrum and the second mass spectrum. The algorithm then compares the signal strength of the peak value of the first mass spectrum to the signal strength of the peak value of the second mass spectrum of the mass spectrum. The relative signal strengths are an indication of the amount of the biomolecule that is present in the first and second samples. A standard containing a known amount of a biomolecule can be analyzed as the second sample to provide better quantify the amount of the biomolecule present in the first sample. In certain embodiments, the identity of the biomolecules in the first and second sample can also be determined.

In one preferred embodiment, at least one epithelial cancer biomarkerlevels are measured by MALDI-TOF mass spectrometry.

Antibodies

The antibodies for use in the present invention can be obtained from a commercial source. Alternatively, antibodies can be raised against the epithelial cancer biomarker polypeptide, or a portion of the epithelial cancer biomarker polypeptide.

Antibodies for use in the present invention can be produced using standard methods to produce antibodies, for example, by monoclonal antibody production (Campbell, A. M., Monoclonal Antibodies Technology: Laboratory Techniques in Biochemistry and Molecular Biology, Elsevier Science Publishers, Amsterdam, the Netherlands (1984); St. Groth et al., J. Immunology, (1990) 35: 1-21; and Kozbor et al., Immunology Today (1983) 4:72). Antibodies can also be readily obtained by using antigenic portions of the protein to screen an antibody library, such as a phage display library by methods well known in the art. For example, U.S. Pat. No. 5,702,892 (U.S.A. Health & Human Services) and WO 01/18058 (Novopharm Biotech Inc.) disclose bacteriophage display libraries and selection methods for producing antibody binding domain fragments.

Detection Kit

The present invention is also directed to commercial kits for the detection and prognostic evaluation of bladder cancer and for the diagnosis of invasive bladder cancer. The kit can be in any configuration well known to those of ordinary skill in the art and is useful for performing one or more of the methods described herein for the detection of at least one epithelial cancer biomarker. The kits are convenient in that they supply many if not all of the essential reagents for conducting an assay for the detection of at least one epithelial cancer biomarker in a biological sample. In addition, the assay is preferably performed simultaneously with a standard or multiple standards that are included in the kit, such as a predetermined amount of at least one epithelial cancer biomarker protein or nucleic acid, so that the results of the test can be quantitated or validated.

The kits include a means for detecting at least one epithelial cancer biomarker levels such as antibodies, or antibody fragments, which selectively bind to at least one epithelial cancer biomarker protein. The diagnostic assay kit is preferentially formulated in a standard two-antibody binding format in which one at least one epithelial cancer biomarker-specific antibody captures the biomarker in a patient sample and another ADAM-specific antibody is used to detect captured at least one epithelial cancer biomarker. For example, the capture antibody is immobilized on a solid phase, e.g., an assay plate, an assay well, a nitrocellulose membrane, a bead, a dipstick, or a component of an elution column. The second antibody, i.e., the detection antibody, is typically tagged with a detectable label such as a calorimetric agent or radioisotope.

In one preferred embodiment, the kit comprises a means for detecting levels of at least one epithelial cancer biomarker in a sample of urine. In a specific embodiment, the kit comprises a "dipstick" with at least one anti-epithelial cancer biomarker antibody or fragments, immobilized thereon, which specifically bind a epithelial cancer biomarker protein. Specifically bound epithelial cancer biomarker protein can then be detected using, for example, a second antibody that is detectably labeled with a calorimetric agent or radioisotope.

In other embodiments, the assay kits may employ (but are not limited to) the following techniques: competitive and non-competitive assays, radioimmunoassay (RIA), bioluminescence and chemiluminescence assays, fluorometric assays, sandwich assays, immunoradiometric assays, dot blots, enzyme linked assays including ELISA, microtiter plates, and immunocytochemistry. For each kit the range, sensitivity, precision, reliability, specificity and reproducibility of the assay are established by means well known to those skilled in the art.

The above described assay kits would further provide instructions for use and a container to hold the urine sample.

All references cited above or below are herein incorporated by reference.

The present invention is further illustrated by the following Examples.

These Examples are provided to aid in the understanding of the invention and are not construed as a limitation thereof.

EXAMPLE 1

Proteomic Analysis of Voided Urine, Bladder Cancer Tissue and Cell Lines for Biomarker Discovery in Transitional Cell Carcinoma Introduction There is a need for new biomarkers to aid in the diagnosis and management of cancers of epithelial origin. Urine can serve as an excellent medium for epithelial cancer biomarker discovery and analysis. Proteomic analysis by two-dimensional polyacrylamide gel electrophoresis (2D PAGE) is one effective tool to analyze the proteome of human specimens. We utilize 2D PAGE to analyze voided urine, human bladder tumor and normal tissue, and human derived bladder cancer cell lines as a method for biomarker discovery.

Methods

Urine

Under IRB approved protocol, we collected voided urine specimens from sixty-three patients prior to diagnostic cystoscopy with biopsy and twenty-two age-matched control patients with no clinical evidence of bladder cancer and no history of malignancy. Total urinary protein was isolated and quantified. Equivalent amounts of protein from individual patients were pooled into three groups: 1. State Ta, high grade; 2. Stage Ta, low grade; 3. Normal controls. Eight patients were included in each group. A total of 40 ng of protein from each group (5 ng per patient) were analyzed and compared by 2D PAGE.

Tissue

Under IRB approved protocol, bladder tumor tissue and normal urothelium were harvested from the cystectomy specimen of a patient with stage T3 N1 M0 transitional cell carcinoma. Tissue specimens were immediately frozen in liquid nitrogen and total protein was then isolated and quantified. 40 ng of protein from each tumor and normal tissue were analyzed and compared by 2D PAGE.

Cell Lines

Fractionated protein was isolated from two previously described cell lines: 1. MGH-U1, cultured from high grade transitional cell carcinoma of the bladder and highly tumorigenic in nude mice; 2. MGH-U4, cultured from a patient with severe urothelial atypia and non-tumorigenic in nude mice. 40 ng of each cytoplasmic, nuclear and membrane protein fractions from each cell line were analyzed and compared by 2D PAGe.

For all above specimens, unique protein spots were isolated and analyzed by liquid chromatography mass spectroscopy-mass spectroscopy (LCMS-MS).

Results

Analysis by 2D PAGE established a number of protein spots at common molecular weights (MW) and isoelectric points (pI) across the 3 groups of urine specimens which represent the common or normal urinary proteome. Similarly, we demonstrated common proteomic spectra for tissue specimens and also for cell lines. The proteomic spectra of urine from Ta high grade patients, tumor tissue and MGH-U1 cell line revealed several similar peptide spots in the MW range 10-15 kD and pI 8-10. We have identified three of these proteins as Cystatin B, an endogenous cysteine proteinase inhibitor, Chaperonin 10, a heat shock protein, and profilin, a cytoskeletal protein.

Conclusions

We demonstrate the discovery of three novel biomarkers for cancers of epithelial origin.

EXAMPLE 1I

Immunostaining for Cystatin B in Bladder Cancer Tissue

Methods

Normal bladder and bladder cancer tissue were immunostained using mouse monoclonal anti-cystatin B antibody and counterstained with Haematoxylin. Immunostaining was performed using the bladder cancer tissue microarray BL801 (US Biomax Inc, Rockville, Md.). The tissues were deparaffinized, endogenous peroxide blocked in 3% hydrogen peroxide in methanol, and microwave antigen retrieval performed using Antigen Unmasking Solution. Blocking was performed using 5% normal horse serum and endogenous biotin blocked using Avidin/Biotin kit. Tissue was incubated with mouse monoclonal anti-cystatin B/Stefin B antibody, clone A6/2 (GeneTex, Inc, San Antonio, Tex.), followed by anti-mouse biotinylated secondary antibody, amplified using ABC kit, and developed using DAB. Tissue was counterstained using Gill's Hematoxylin #3 (Sigma-Aldrich, St. Louis, Mo.), and blued using Tacha's Bluing Solution (Biocare, Concord, Calif.). All reagents were purchased from Vector Laboratories, Burlingame, Calif., except where noted. All images were captured at equal exposure time.

Results

The levels of Cystatin B in samples from individuals with bladder cancer were significantly higher than the levels observed in samples of normal bladder tissue.

What is claimed is:

1. A method for facilitating the diagnosis of bladder cancer in a patient consisting of:
   a. obtaining a urine sample from the patient; and
   b. detecting the presence or absence of Cystatin B in the urine sample, wherein the presence of Cystatin B epithelial cancer biomarker is indicative of bladder cancer.

2. A method for diagnosing bladder cancer in a patient consisting of:
   (a) measuring the levels of Cystatin B present in a urine sample obtained from the patient, a test sample;
   (b) comparing the level of Cystatin B in the test sample with the level of
   Cystatin B epithelial cancer biomarker present in a control sample; wherein a higher level Cystatin B in the test sample as compared to the level of Cystatin B in the control sample is indicative of bladder cancer.

3. A method for diagnosing invasive bladder cancer in a patient consisting of:
   a. measuring the levels of Cystatin B present in a urine sample obtained from the patient, a test sample;
   b. comparing the level of Cystatin B in the test sample with the level of Cystatin B present in a non-invasive control sample;
   wherein a higher level Cystatin B in the test sample as compared to the level of Cystatin B in the non-invasive control sample is indicative of invasive bladder cancer.

4. The method of claim 1, wherein the presence or absence of Cystatin B is detected using an antibody-based binding moiety which specifically binds to at least one epithelial cancer biomarker.

5. The method of claim 2, wherein the level of Cystatin B is measured by measuring the protein level of Cystatin B protein.

6. The method of claim 5, wherein the protein level of Cystatin B is measured by a method comprising the steps of:
   a. contacting the test sample, or preparation thereof, with an antibody-based binding moiety which specifically binds Cystatin B to form an antibody Cystatin B complex; and
   b. detecting the presence of the complex, thereby measuring the level of Cystatin B present.

7. The method according to claim 4, wherein the antibody-based binding moiety is labeled with a detectable label.

8. The method according to claim 7, wherein the label is selected from the group consisting of a radioactive label, a hapten label, a fluorescent label, and an enzymatic label.

9. The method according to claim 4 wherein the antibody-based binding moiety is an antibody.

10. The method according to claim 9, wherein the antibody is a monoclonal antibody.

11. A method for assessment of bladder cancer, the method consisting of:
    a. assaying for Cystatin B in a urine sample obtained from a subject; and
    b. determining whether Cystatin B is present at a level higher than a predetermined level, thereby indicating whether the subject is at an increased risk of bladder cancer progression.

12. The method of claim 11 wherein the predetermined level is based on the level of Cystatin B normally found in urine samples of healthy subjects.

13. The method of claim 11 wherein the predetermined level is based on a prior measurement of the subject's Cystatin B level.

14. The method of claim 11 wherein the predetermined level is based on the subject's Cystatin B level prior to treatment.

15. The method of claim 11 wherein the subject's Cystatin B level is monitored over time.

16. The method of claim 11 wherein the cancer progression is a recurrence of cancer.

17. The method of claim 11 wherein the cancer progression is an increase of metastatic activity.

18. The method of claim 11 wherein the cancer progression is a progression in cancer grade or stage.

19. The method of claim 11 wherein the Cystatin B protein is assayed for by an immunoassay or by mass spectrometry.

* * * * *